(12) United States Patent
Wannamaker et al.

(10) Patent No.: US 8,329,662 B2
(45) Date of Patent: Dec. 11, 2012

(54) PRODRUG OF AN ICE INHIBITOR

(75) Inventors: Marion W. Wannamaker, Bolton, MA (US); Robert J. Davies, Watertown, MA (US)

(73) Assignee: Vertexd Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/210,712

(22) Filed: Aug. 16, 2011

(65) Prior Publication Data

US 2011/0301096 A1    Dec. 8, 2011

Related U.S. Application Data

(62) Division of application No. 12/165,838, filed on Jul. 1, 2008, now Pat. No. 8,022,041, which is a division of application No. 09/860,750, filed on May 18, 2001, now Pat. No. 7,417,029.

(60) Provisional application No. 60/205,439, filed on May 19, 2000.

(51) Int. Cl.
    *A61K 38/05*    (2006.01)

(52) U.S. Cl. .................................. 514/21.91; 514/20.1

(58) Field of Classification Search ................ 514/21.91, 514/20.1
     See application file for complete search history.

(56) References Cited

U.S. PATENT DOCUMENTS

| | | |
|---|---|---|
| 4,465,679 A | 8/1984 | Huang et al. |
| 5,008,245 A | 4/1991 | Digenis et al. |
| 5,055,451 A | 10/1991 | Krantz et al. |
| 5,158,936 A | 10/1992 | Krantz et al. |
| 5,411,985 A | 5/1995 | Bills et al. |
| 5,416,013 A | 5/1995 | Black et al. |
| 5,430,128 A | 7/1995 | Chapman et al. |
| 5,434,248 A | 7/1995 | Chapman et al. |
| 5,462,939 A | 10/1995 | Dolle et al. |
| 5,463,124 A | 10/1995 | Jacobi et al. |
| 5,486,623 A | 1/1996 | Zimmerman et al. |
| 5,498,616 A | 3/1996 | Mallamo et al. |
| 5,498,695 A | 3/1996 | Daumy et al. |
| 5,519,113 A | 5/1996 | Jendralla et al. |
| 5,552,400 A | 9/1996 | Dolle et al. |
| 5,565,430 A | 10/1996 | Dolle et al. |
| 5,585,357 A | 12/1996 | Dolle et al. |
| 5,585,486 A | 12/1996 | Dolle et al. |
| 5,639,745 A | 6/1997 | Dolle et al. |
| 5,656,627 A | 8/1997 | Bemis et al. |
| 5,670,494 A | 9/1997 | Dolle et al. |
| 5,710,153 A | 1/1998 | Ohmoto et al. |
| 5,716,929 A | 2/1998 | Bemis et al. |
| 5,756,466 A | 5/1998 | Bemis et al. |
| 5,847,135 A | 12/1998 | Bemis et al. |
| 5,869,519 A | 2/1999 | Karanewsky et al. |
| 5,874,424 A | 2/1999 | Batchelor et al. |
| 5,877,197 A | 3/1999 | Karanewsky et al. |
| 5,973,111 A | 10/1999 | Bemis et al. |
| 6,136,834 A | 10/2000 | Ohmoto et al. |
| 6,376,484 B1 | 4/2002 | Ohmoto et al. |
| 6,531,474 B1 | 3/2003 | Wannamaker et al. |
| 2002/0013278 A1 | 1/2002 | Wannamaker et al. |

FOREIGN PATENT DOCUMENTS

| | | |
|---|---|---|
| EP | 04104111 A2 | 1/1991 |
| EP | 0417721 B1 | 3/1991 |
| EP | 0519748 B1 | 12/1992 |
| EP | 0525420 B1 | 2/1993 |
| EP | 0528487 A2 | 2/1993 |
| EP | 0529713 A1 | 3/1993 |
| EP | 0533226 A2 | 3/1993 |
| EP | 0533350 B1 | 3/1993 |
| EP | 0547699 A1 | 6/1993 |
| EP | 0618223 A2 | 10/1994 |
| EP | 0623592 B1 | 11/1994 |
| EP | 0623606 B1 | 11/1994 |
| EP | 0644197 B1 | 3/1995 |
| EP | 0644198 A1 | 3/1995 |
| EP | 0810221 A1 | 3/1997 |
| EP | 0135349 B1 | 9/2009 |
| WO | 9115577 A1 | 10/1991 |
| WO | 9305071 A1 | 3/1993 |
| WO | 9309135 A1 | 5/1993 |
| WO | 9314777 A1 | 8/1993 |

(Continued)

OTHER PUBLICATIONS

M. Ator, "Peptide and Non-peptide inhibitors of interleukin-1Beta Converting Enzyme" Cambridge Healthtech Institute Inflammatory Cytokine Antagonists Targets, Strategies, and Indication, p. 1-15 (1994).

(Continued)

*Primary Examiner* — David Lukton
(74) *Attorney, Agent, or Firm* — Jennifer G. Che

(57) ABSTRACT

This invention describes an ICE inhibitor prodrug (I) having good bioavailability.

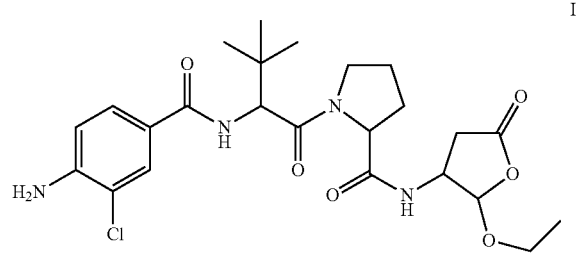

Compound I is useful for treating IL-1 mediated diseases such as rheumatoid arthritis, inflammatory bowel disease, Crohn's disease, ulcerative colitis, inflammatory peritonitis, septic shock, pancreatitis, traumatic brain injury, organ transplant rejection, osteoarthritis, asthma, psoriasis, Alzheimer's disease, myocardial infarction, congestive heart failure, Huntington's disease, atherosclerosis, atopic dermatitis, leukemias and related disorders, myelodysplastic syndrome, uveitis or multiple myeloma.

2 Claims, No Drawings

FOREIGN PATENT DOCUMENTS

| | | |
|---|---|---|
| WO | 9316710 A1 | 9/1993 |
| WO | 9400154 A1 | 1/1994 |
| WO | 94/03480 A1 | 2/1994 |
| WO | 9500160 A1 | 1/1995 |
| WO | 9501592 A1 | 2/1995 |
| WO | 9526958 A1 | 10/1995 |
| WO | 95/31535 A1 | 11/1995 |
| WO | 9529672 A1 | 11/1995 |
| WO | 9535308 A1 | 12/1995 |
| WO | 9535367 A1 | 12/1995 |
| WO | 9603982 A1 | 2/1996 |
| WO | 9625408 A1 | 8/1996 |
| WO | 9630395 A2 | 10/1996 |
| WO | 9633209 A1 | 10/1996 |
| WO | 9640647 A1 | 12/1996 |
| WO | 9707805 A1 | 3/1997 |
| WO | 9708174 A1 | 3/1997 |
| WO | 9722619 A2 | 6/1997 |
| WO | 9724339 A1 | 7/1997 |
| WO | 9804539 A1 | 2/1998 |
| WO | 9810778 A1 | 3/1998 |
| WO | 9811109 A1 | 3/1998 |
| WO | 9811129 A1 | 3/1998 |
| WO | 9849189 A1 | 11/1998 |
| WO | 9947545 A2 | 9/1999 |

OTHER PUBLICATIONS

MacKenzie, et al., "An inhibitor of the Interleukin Processing Enzyme Blocks IL-1 Release and Reduces Pyrexia and Acute Inflammation" Inflammation Research Associate 7th Internat. Conf. W42 (1994).

Prasad et al., "P1 Aspartate-Based Peptide Alpha-Arylacyloxy- and alpha-aryloxymethyl ketones as potent time—dependent inhibitors of Interleukin-1beta converting enzyme" Am. Chem. Soc. Abs. 24th Med. Chem. Symp. 66, (1994).

T. Graybill, et al., "The Preparation and Evaluation of Peptidic Aspartyl Hemiacetals as Reversible Inhibitors of ICE", Am. Chem Soc. Abs. (206th Natl. Mtg.), MEDI 235, (1993).

AF Spatola, "Chemistry and Biochemistry of Amino Acids Peptides, and Proteins", 7, ch. 5, pp. 267-281, Weinstein, B., ed., Marcel Dekker, Inc., New York, (1983).

Apr. 2, 2002 Office Action from U.S. Appl. No. 09/665,503.

Dec. 14, 2001 Office Action from U.S. Appl. No. 09/665,503.

Jul. 2, 2001 Office Action from U.S. Appl. No. 09/665,503.

I. Fauszt et al., "Inhibition of Interleukin-1beta Converting Enzyme by Peptide Derivatives," Proc. of the 13th Am. Peptide Symp., Jun. 20-25, 1993; Hodges, R.S. and Smith, J.A., Eds., Peptides, 589-591, (1994).

S. Schmidt et al., "Synthesis and Evaluation of Aspartyl alpha-Chloro-, alpha-Aryloxy-, and alpha-Arylacyloxymethyl Ketones as Inhibitors of Interleukin-1beta Converting Enzyme," Am. Chem. Soc. Abs. (208th Natl. Mtg.), MEDI 4, (1994).

Apr. 2, 2007 Office Action from U.S. Appl. No. 10/314,103.

Jun. 28, 2006 Office Action from U.S. Appl. No. 10/314,103.

Oct. 5, 2005 Office Action from U.S. Appl. No. 10/314,103.

Dec. 29, 2004 Office Action from U.S. Appl. No. 10/314,103.

Apr. 7, 2004 Office Action from U.S. Appl. No. 10/314,103.

Apr. 1, 2002 Office Action from U.S. Appl. No. 09/665,503.

A.M.M. Mjalli et al., "Activated Ketones as Potent Reversible Inhibitors of Interleukin-1β Converting Enzyme", Bioorg. Med. Chem. Lett., 4, 1965-1968, (1994).

B. Miller et al., Inhibition of Mature IL-1β Production in Murine Macrophages and a Murine Model of Inflammation by WIN 67694, an Inhibitor of IL-1β Converting Enzyme:, J. Immunol., 154, 1331-1338, (1995).

Wannamaker, et al.; "(S)-1-((S)-2-{[1-(4-Amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765), an Orally Available Selective Interleukin (IL)-Converting Enzyme/Caspase-1 Inhibitor, Exhibits Potent Anti-Inflammatory Activities by Inhibiting the Release of IL-1β and IL-18", JPET; 321:509-516 (2007).

Tocci, PubMed Abstract Vitam. Horm. 53:27-63, (1997).

Simone, Oncology: Introduction, Cecil Textbook of Medicine, 20th Edition, vol. 1,1004-1010, (1996).

M.D. Mullican et al., "The Synthesis and Evaluation of Peptidyl Aspartly Aldehydes as Inhibitors of ICE", Bioorg. Med. chem. Lett., 4, 2359-2364, (1994).

Okamoto et al., Peptide Based ICE Inhibitors: Synthesis, Structure Activity Relationships and Crystallographic Study of the ICE-inhibitor Complex, Chem. Pharm. Bull., 47(1), 11-21, (1999).

Ravizza T, Lucas SM, Balosso S, Bernardino L, Ku G, Noe F, Melva J, Randle JC, Allan S, Vezzani, "A. Abstract Inactivation of caspase-1 in rodent brain: a novel anticonvulsive strategy". Epilepsia, 47(7):1160-8, (2006).

Stack JH, Beaumont K, Larsen PD, Straley KS, Henkel GW, Randle JC, Hoffman HM. "Free Full Text IL-converting enzyme/caspase-1 inhibitor VX-765 blocks the hypersensitive response to an inflammatory stimulus in monocytes from familial cold autoinflammatory syndrome patients.", J Immunol., 15;175 (4):2630-4, (2005).

Thakur, et al., "Caspase-1 Inhibitor Reduces Severity of Pseudomonas aeruginosa Keratitis in Mice," Invest Ophthalmol Vis Sci., 45:3177-3184, (2004).

Karanewsky et al., Conformationally Constrained Inhibitors of Caspase-1(Interleukin-1β Converting Enzyme) and of the Human CED-3 Homologue Caspase-3 (CPP32, Apopain), bioorganic & Med. Chem. Ltrs. 8, 2757:2762 (1998).

Strasser A., "The Role of Bim, a Proapoptotic BH3-Only Member of the Bcl-2 Family, in Cell-Death Control", Annals of New York Academy of Sciences, 917, 541-548, (2000).

Van Den Brande, Jan M.H., "Treating Crohn's Disease by Inducing T Lymphocyte Apoptosis", Annals of the New York Academy of Sciences, 973, 166-180, (2002).

Kacinski B M, "Apoptosis and Cutaneous T Cell Lymphoma", Annals of the New York Academy of Sciences, 941, 194-199, (2001).

Tsuchiyama Y., "Efficacy of Galectins in the Amelioration of Nephrotoxic serum nephritis in Wistar Kyoto Rats", Kidney International 58(5), 1941-1952, (2002).

Li X.C., "The role of T Cell apoptosis in transplantation tolerance", Current Opinion in Immunology, 12(5) 522-527 (2000).

Bednarski Jeffrey J., "Attenuation of autoimmune Disease in Fas-Deficient Mice by Treatment with a Cytotoxic Benzodiazepine", Arthritis and Rheumatism, 48(3) 757-766 (2003).

Kanegane, Hirokazu, "Autoimmune lymphoproliferative syndrome presenting with glomerulonephritis" Pediatr. Nephrol., 18:454-456 (2003).

K. Chapman, "Synthesis of a Potent, Reversible Inhibitor of Interleukin-1 Converting Enzyme", Bioorg. Med. Chem. Lett., 2, 613-618, (1992).

Dolle et al., "Aspartyl-((Diphenylphosphinyl)oxy)methyl Ketones as Novel Inhibitors of Interleukin-1β Converting Enzyme. Utility of the Diphenyphosphinic Acid Leaving Group for the Inhibition of Cysteine Proteases", J. Med. Chem., 38, 220-222, (1995).

Dolle et al., "Aspartyl-((1-Phenyl-3-(trifluoromethyl)-pyrazol-5-yl)oxy)methyl Ketones as Interleukin-1β converting Enzyme Inhibitors. Significance of the P1 and P3 Amido Nitrogens for Enzyme-Peptide Inhibitor Binding", J. Med. Chem., 37, 3863-3865, (1994).

Dolle et al., "P1 Aspartate-Based Peptide-((2,60Dichlorobenzoyl)oxy)methyl) Ketones as Potent Time-Dependent Inhibitors of Interleukin-1β Converting Enzyme", J. Med. Chem., 37, 563-564, (1994).

P. Edwards et al., "Design, Synthesis, and Kinetic Evaluation of a Unique Class of Elastase Inhibitors, the Peptidyl-Ketobenzoxazoles, and the X-ray Crystal Structure of the Covalent Complex Between Porcine Pancreatic Elastase and Ac-Ala-Pro-Val020Benzoxazole", J. Am. Chem. Soc., 114, 1854-1863, (1992).

P.R. Elford et al., "Reduction of Inflammation and Pyrexia in the Rat by Oral Administration of SDZ 224-015, an Inhibitor of the Interleukin-1β Converting Enzyme", Br. J. Pharmacology, 115, 601-606, (1995).

T.P.D. Fan et al., "Stimulation of Angiogenesis by Substance P and Interleukin-1 in the Rat and its Inhibition by NK1 or Interleukin-1 Receptor Antagonists", Br. J. Pharmacol., 10, 43-49, (1993).

D. Fletcher et. al., "A Stnthetic Inhibitor of Interleukin-1β Converting Enzyme Prevents Endotoxin-Induced Interleukin-1β Production in Vitro and in Vivo", J. Interfer. Cytokine Res., 15, 243-248, (1995).

T. Graybill et al., "Preparation and Evaluation of peptidic Aspartyl Hemiacetals as Reversible Inhibitors of Interleukin-1β Converting Enzyme (ICE)", Int. J. peptide Protein Res., 44, 173-182, (1994).

S. Hanessian et al., "Design and Synthesis of a Prototype Model Antagonist of Tachykinin NK-2 Receptor", Bioorg. Med. Chem. Lett, 4(11), 1397-1400, (1994).

R.B. Layzer, "Degenerative Diseases of the Nervous System", Cecil Textbook of Medicine, 20th Edition, vol. 2, 2050-2057, (1996).

A. MacKenzie et al., "An Inhibitor of the Interleukin-1β Processing Enzyme Blocks IL-1 Release and reduces Pyrexia and Acute Inflammation", Inflammation Research Association (7th Internat. Conf.), W42, (1994).

Abstract of Ando, R., WO96/25408 issued Aug. 1995.

Abstract of Ohmoto, K., WO97/24339 issued Jul. 1997.

Abstract of Aibe, K. WO98/01133 issued Jan. 1998.

Abstract of Ando, R. WO98/04539 issued Feb. 1998.

Y. Okamoto et al., "Peptide Based Interleukin-1β Converting Enzyme (ICE) Inhibitors: Synthesis, Structure Activity Relationships and Crystallographic Study of the ICE-inhibitor Complex," Chem. Pharm. Bull (Tokyo), 47(1):11-21, (1999).

M. Pennington & N. Thornberry, "Synthesis of a Fluorogenic Interleuking-1β Converting Enzyme Substrate Based on Resonance Energy Transfer," pept. Res., 7, 72-76, (1994).

C. Prasad et al., "P1 Aspartate-Based Peptide-Arlacyloxy-and-Aryloxymethyl Ketones as Potent Time Dependent Inhibitors of Interleukin 1β Converting Enzyme," Am. Chem. Soc. Abs. (24th Med. Chem. Symp.) 66, (1994).

C. Ray et al., "Viral Inhibition of Inflammation: Cowpox Virus Encodes as Inhibitor of the Interleukin-1β Converting Enzyme," Cell 69, 597-604, (1992).

L. Reiter, "Peptide p-Nitroanilide Substrates of Interleukin-1β Converting Enzyme," Int. J. Pept. Protein Res., 43, 87-96, (1994).

L. Revez et al., "Synthesis of P1 Aspartate-Based Peptide Acyloxymethyl and Fluoromethyl Ketones as Inhibitors of Interleukin-1β Converting Enzyme," Tetrahedron Lett., 35 (52), 9693-9696, (1994).

R.P. Robinson and K.M. Donahue, "Synthesis of a Peptidyl Difluoro Ketone Bearing and Aspartic Acid Side Chain: An Inhibitor of Interleukin-1β Convertin Enzyme," J. Org. Chem., 57, 7309-7314, (1992).

J.V. Simone, "Oncology: Introduction," Cecil Textbook of Medicine, 20th Edition, vol. 1, 1004-1010, (1996).

P. Sleath et al., "Substrate Specificity of the Protease that Processes Human Interleukin-1β ," J. Biol. Chem, 265, 14526-14528, (1990).

N. Thornberry et al., "Inactivation of Interleukin-1β Converting Enzyme by Peptide (Acyloxy)methyl Ketones," Biochemistry, 33, 3934-3940, (1994).

J. Uhl et al., "Secretion of Human Monocyte Mature IL-1β: Optimization of Culture Conditions and Inhibition by ICE Inhibitors," Inflammation Res., 44, S211-S212, (1995).

P. Villa et al., "Caspases and Caspase Inhibitors," Trends in Biochemical Sciences, 22, 388-393, (1997).

M.A. Ator and R.E. Dolle, "Interleukin-1β Converting Enzyme: Biology and The Chemistry of Inhibitors," Curr. Pharm. Design, 1, 191-210, (1995).

A.M.M. Mjalli et al., "Phenylalkyl Ketones as Potent Reversible Inhibitors of Interleukin-1β Converting Enzyme," Bioorganic & Medicinal Chemistry Letters., 3, 2689-2692, (1993).

Livingston, D.J., "In Vitro and in Vivo Studies of ICE Inhibitors," J. Cell. Biochem. (1997) 64, 19-26.

Paszkowski, A.S. et al., "Therapeutic Application of Caspase 1/Interleukin-1beta-Converting Enzyme Inhibitor Decreases the Death Rate in Severe Acute Experimental Pancreatitis," Annuals of Surgery (2002) 235(1), 68-76.

Ku, G., et al., "Interleukin-1β Converting Enzyme Inhibition Blocks Progression of Type II Collagen-Induced Arthritis in Mice," Cytokine, 8, pp. 337-386 (1996).

Rouquet, N., et al., "ICE inhibitor YVADcmk is a potent therapeutic agent against in vivo liver apoptosis," Current Biology (1996) 6(9), 1192-1195.

Siegmund, G., "Interleukin-1β converting enzyme (caspase-1) in intestinal inflammation," Biochem. Pharmacol. (2002), 65, 1-8.

Hotchkiss, R.S., et al., "Caspase inhibitors improve survival in sepsis: a critical role of the lymphocyte," Nature Immunol. (2000) 1, 496-50.

Grobmyer, S.R. et al., "Peptidomimetic Fluoromethylketone Rescues Mice from Lethal Endotoxic Shock," Molecular Medicine (1999) 5, 585-594.

Antonopoulos, C. et al., "Functional caspase-1 is required for Langerhans cell migration and optimal contact sensitization in mice," J. Immunol. (2001) 166, 3672-7.

Hara, H. et al., "Inhibition of interleukin 1β converting enzyme family proteases reduces ischenmic and exitotoxic neuronal damage," Proc. Natl. Acad. Sci. USA, (1997), 94, 2007-2012.

Yakovlev, A.G. et al., "Activation of CPP32-Like Caspases Contributes to Neuronal Apoptosis and Neurological Dysfunction after Traumatic Brain Injury," J. Neuroscience (1997) 17(19), 7415-7424.

Knoblach, S.M. et al., "Multiple Caspases are Activated after Traumatic Brain Injury: Evidence for Involvement in Functional Outcome," J. Neurotrauma (2002) 19, 1155-1170.

Endres, M. et al., "Attenuation of Delayed Neuronal Death After Mild Focal Ischemia in Mice by Inhibition of the Caspase Family," J. Cerebral Blood Flow and Metabolism (1998) 18, 238-247.

Pomerantz, B.J. et al., "Inhibition of caspase 1 reduces human myocardial ischemic dysfunction via inhibition of IL-18 and IL-1β," PNAS (2001) 98(5), 2871-2876.

Yaoita, H. et al., "Attenuation of Ischemia/Reperfusion Injury in Rats by a Caspase Inhibitor," Circulation (1998) 97(3), 276-281.

Li, M. et al., "Functional Role of Caspase-1 and Caspase-3 in an ALS Transgenic Mouse Model," Science, 288, pp. 335-339 (2000).

Friedlander, R.M. et al., "Inhibition of ICE Slows ALS in Mice" Nature, 388, pp. 31 (1997).

Ilzecka, J. et al., "Interleukin-1β Converting Enzyme/Caspase 1 (ICE/Caspase-1) and Soluble APO-1/Fas/CD 95 Receptor in Amyotrophic Lateral Sclerosis Patients," Acta Neurolog. Scand., 103., 103, pp. 255-258 (2001).

Furlan, R. et al., "Caspase-1 Regulates the Inflammatory Process Leading to Autoimmune Demyelination," J. Immunol. (1999) 163, 2403-2409.

Schierle, G.S. et al., "Caspase Inhibition Reduces Apoptosis and Increases Survival of Nigral Transplants," Nature Medicine (1999) 15(1), 97-100.

Nicoletti, F. et al., "Protection from experimental autoimmune diabetes in the non-obese diabetic mouse with soluble interleukin-1 receptor," Eur. J. Immunol. (1994) 24, 1843-1847.

Bataille, R. et al., "The critical role of interleukin-6, interleukin-1B and macrophage colony-stimulating factor in the pathogenesis of bone lesions in multiple myelmoma," Int. J. Clin. Lab Res. (1992) 21, 283-287.

Ankersmit HJ, Weber T., Auer J., Roth G., Brunner M., Kvas E., Moser B., Speitzer S., Lassnig E., Maurer E., Hartl P., Wolner E., Boltz-Nitulescu G., Eber B., "Increased serum concentrations of soluble CD95/Fas and caspase 1.ICE in patients with acute angina" Heart 2004; 90: 151-154.

Gagliardini, V. et al., "Prevention of Vertebrate Neuronal Death by the crmA Gene," Science (1994) 263, 826-828.

Arndt, P.G. et al., "Expression of Interleukin-18 in the Lung after Endotoxemia or Hemorrhage-Induced Acute Lung Injury," Am. J. Respir. Cell Mol. Biol. (2000) 22, 708-713.

McCarthy, Jr., P.L. et al., "Inhibition of Interleukin-1 by an Interleukin-1 Receptor Antagonist Prevents Graft-Versus Host Disease," Blood (1991) 78, 1915-1918.

Alcocer-Valera, J. et al., "Spontaneous production of, and defective response to interleukin-1 by peripheral blood mononuclear cells from patients with sceroderma," Clin. Exp. Immunol. (1985), 59, 666-672.

Kimble, R.B. et al., "Persistent Bone-Sparing Effect of Interleukin-1 Receptor Antagonist: A Hypothesis on the Role of IL-1 in Ovariectomy-Induced Bone Loss," (1994), 55, 260-265.

Ona et al., "Inhibition of caspase-1 slows disease progression in a mouse model of Huntington's disease," Nature, 1999, May 20; 399, (6733): 263-7.

PRODRUG OF AN ICE INHIBITOR

CROSS REFERENCE TO RELATED APPLICATIONS

This application is a divisional of application 12/165838, filed Jul. 01, 2008, now U.S. Pat. No. 8,022,041, which is a divisional of application 09/860750, filed May 18, 2001, now U.S. Pat. No. 7,417,029, which claims priority to provisional application 60/205439, filed May 19, 2000.

TECHNICAL FIELD OF THE INVENTION

The present invention relates to a novel interleukin-1β converting enzyme (ICE) inhibitor in its prodrug form. The compound and pharmaceutical compositions thereof are useful as agents to treat interleukin-l- (IL-1), apoptosis-, interferon-γ inducing factor- (IL-18), or interferon-γ (IFN-γ) mediated diseases, including inflammatory diseases, autoimmune diseases, destructive bone disorders, proliferative disorders, infectious diseases, and degenerative diseases. This invention also relates to methods for inhibiting ICE activity and decreasing IL-18 production and IFN-γ production and methods for treating interleukin-1, apoptosis-, and interferon-γ- mediated diseases using the compositions of this invention.

BACKGROUND OF THE INVENTION

Interleukin-1 (IL-1) is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45-56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum.* 26, 975, (1983); Pettipher, E. J. et al., *Proc. Natl. Acad. Sci. USA* 71, 295 (1986); Arend, W. P. and Dayer, J. M., *Arthritis Rheum.* 38, 151 (1995). IL-1 is also a highly potent bone resorption agent. Jandiski, J. J., *J. Oral Path* 17, 145 (1988); Dewhirst, F. E. et al., *J. Immunol.* 8, 2562 1985). It is alternately referred to as "osteoclast activating factor" in destructive bone diseases such as osteoarthritis and multiple myeloma. Bataille, R. et al., *Int. J. Clin. Lab. Res.* 21(4), 283 (1992). In certain proliferative disorders, such as acute myelogenous leukemia and multiple myeloma, IL-1 can promote tumor cell growth and adhesion. Bani, M. R., *J. Natl. Cancer Inst.* 83, 123 (1991); Vidal-Vanaclocha, F., *Cancer Res.* 54, 2667 (1994). In these disorders, IL-1 also stimulates production of other cytokines such as IL-6, which can modulate tumor development (Tartour et al., *Cancer Res.* 54, p. 6243 (1994). IL-1 is predominantly produced by peripheral blood monocytes as part of the inflammatory response and exists in two distinct agonist forms, IL-1α and IL-1β. Mosely, B. S. et al., *Proc. Nat. Acad. Sci.*, 84, pp. 4572-4576 (1987); Lonnemann, G. et al., *Eur. J. Immunol.*, 19, pp. 1531-1536 (1989).

IL-1β is synthesized as a biologically inactive precursor, pro-IL-1β. Pro-IL-1β lacks a conventional leader sequence and is not processed by a signal peptidase. March, C. J., *Nature*, 315, pp.641-647 (1985). Instead, pro-IL-1β is cleaved by interleukin-1β converting enzyme (ICE) between Asp-116 and Ala-117 to produce the biologically active C-terminal fragment found in human serum and synovial fluid. Sleath, P. R., et al., *J. Biol. Chem.*, 265, pp.14526-14528 (1992); A. D. Howard et al., *J. Immunol.*, 147, pp:2964-2969 (1991). ICE is a cysteine protease localized primarily in monocytes. It converts precursor IL-1β to the mature form. Black, R. A. et al., *FEBS Lett.*, 247, pp.386-390 (1989); Kostura, M. J. et al., *Proc. Natl. Acad. Sci. U.S.A.*, 86, pp.5227-5231 (1989). Processing by ICE is also necessary for the transport of mature IL-1β through the cell membrane.

ICE (or caspase-1) is a member of a family of homologous enzymes called caspases. These homologs have sequence similarities in the active site regions of the enzymes. Such homologs (caspases) include TX (or $ICE_{rel-II}$ or ICH-2) (caspase-4) (Faucheu, et al., *EMBO J.*, 14, p. 1914 (1995); Kamens J., et al., *J. Biol. Chem.*, 270, p. 15250 (1995); Nicholson et al., *J. Biol. Chem.*, 270 15870 (1995)), TY (or $ICE_{rel-III}$) (caspase-5) (Nicholson et al., *J. Biol. Chem.*, 270, p. 15870 (1995); ICH-1 (or Nedd-2) (caspase-2) (Wang, L. et al., *Cell*, 78, p. 739 (1994)), MCH-2 (caspase-6), (Fernandes-Alnemri, T. et al., *Cancer Res.*, 55, p. 2737 (1995), CPP32 (or YAMA or apopain) (caspase-3) (Fernandes-Alnemri, T. et al., *J. Biol. Chem.*, 269, p. 30761 (1994); Nicholson, D. W. et al., *Nature*, 376, p. 37 (1995)), CMH-1 (or MCH-3) (caspase-7) (Lippke, et al., *J. Biol. Chem.*, 271(4), p1825-1828 (1996)); Fernandes-Alnemri, T. et al., *Cancer Res.*, (1995)), Mch5 (caspase-8) (Muzio, M. et.al., *Cell* 85(6), 817-827, (1996)), MCH-6 (caspase-9) (Duan, H. et.al., *J. Biol. Chem.*, 271(34), p. 16720-16724 (1996)), Mch4 (caspase-10) (Vincenz, C. et.al., *J. Biol. Chem.*, 272, p. 6578-6583 (1997); Fernandes-Alnemri, T. et.al., *Proc. Natl. Acad. Sci.* 93, p. 7464-7469 (1996)), Ich-3 (caspase-11) (Wang, S. et.al., *J. Biol. Chem.*, 271, p. 20580-20587 (1996)), mCASP-12 (caspase-12), (Van de Craen, M. et.al., *FEBS Lett.* 403, p. 61-69 (1997); Yuan, Y. and Miura, M. *PCT Publication* WO95/00160 (1995)), ERICE (caspase-13), (Humke,. E. W., et.al., *J. Biol. Chem.*, 273(25) p. 15702-15707 (1998)), and MICE (caspase-14) (Hu, S. et.al., *J. Biol. Chem.*, 273(45) p. 29648-29653 (1998)).

Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., *Nature*, 371, p. 346 (1994).

Caspases also appear to be involved in the regulation of programmed cell death or apoptosis. Yuan, J. et al., *Cell*, 75, pp.641-652 (1993); Miura, M. et al., *Cell*, 75, pp. 653-660 (1993); Nett-Fiordalisi, M. A. et al., *J. Cell Biochem.*, 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, *Science*, 259, pp. 760-762 (1993); Gagliardini, V. et al., *Science*, 263, pp. 826-828 (1994). Inhibition of caspases have also recently been shown to be effective in a murine model of amylotropic lateral sclerosis. Li, M. et al.; *Science*, 288, pp. 335-339 (2000). Therapeutic applications for inhibition of apoptosis may include, among others, treatment of Alzheimer's disease, Parkinson's disease, stroke, myocardial infarction, spinal atrophy, and aging.

ICE has been demonstrated to mediate apoptosis (programmed cell death) in certain tissue types. Steller, H., *Science*, 267, p. 1445 (1995); Whyte, M. and Evan, G., *Nature*, 376, p. 17 (1995); Martin, S. J. and Green, D. R., *Cell*, 82, p. 349 (1995); Alnemri, E. S., et al., *J. Biol. Chem.*, 270, p. 4312 (1995); Yuan, J. *Curr. Opin. Cell Biol.*, 7, p. 211 (1995). A transgenic mouse with a disruption of the ICE gene is deficient in Fas-mediated apoptosis (Kuida, K. et al., *Science* 267, 2000 (1995)). This activity of ICE is distinct from its role as the processing enzyme for pro-IL-1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp.768-774 (1992). The ICE proenzyme has been divided into several functional domains: a prodomain (p14), a p22/20 subunit, a polypeptide linker and a p10 subunit. *Thornberry et al., supra*; Casano et al., *Genomics*, 20, pp. 474-481 (1994).

Full length p45 has been characterized by its cDNA and amino acid sequences. PCT patent applications WO 91/15577 and WO 94/00154. The p20 and p10 cDNA and amino acid sequences are also known. *Thornberry et al., supra*. Murine and rat ICE have also been sequenced and cloned. They have high amino acid and nucleic acid sequence homology to human ICE. Miller, D. K. et al., *Ann. N.Y. Acad. Sci.*, 696, pp. 133-148 (1993); Molineaux, S. M. et al., *Proc. Nat. Acad. Sci.*, 90, pp. 1809-1813 (1993). The three-dimensional structure of ICE has been determined at atomic resolution by X-ray crystallography. Wilson, K. P., et al., *Nature*, 370, pp. 270-275 (1994). The active enzyme exists as a tetramer of two p20 and two p10 subunits.

Recently, ICE and other members of the ICE/CED-3 family have been linked to the conversion of pro-IL-18 to IL-18 or to the production of IFN-γ in vivo (PCT application PCT/US96/20843, publication no. WO 97/22619, which is incorporated herein by reference). IL-18 is synthesized in vivo as the precursor protein "pro-IL-18".

Interleukin-18 (IL-18), formerly interferon-gamma inducing factor, (IGIF) is an approximately 18-kDa polypeptide that stimulates T-cell production of interferon-gamma (IFN-γ-). IL-18 is produced by activated Kupffer cells and macrophages in vivo and is exported out of such cells upon endotoxin stimulation. Like IL-1β, IL-18 is synthesized as a biologically inactive precursor molecule lacking a single peptide, which requires cleavage into an acitve, mature molecule by IL-1β converting enzyme. Dinerello, C. A. *Methods*, 19, pp 121-132 (1999). Thus, a compound that decreases IL-18 production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (F. Belardelli, *APMIS*, 103, p. 161 (1995)). IFN-γ exerts its effects in part by modulating the expression of genes through the STAT and IRF pathways (C. Schindler and J. E. Darnell, *Ann. Rev. Biochem.*, 64, p. 621 (1995); T. Taniguchi, *J. Cancer Res. Clin. Oncol.*, 121, p. 516 (1995)).

Mice lacking IFN-γ or its receptor have multiple defects in immune cell function and are resistant to endotoxic shock (S. Huang et al., *Science*, 259, p.1742 (1993); D. Dalton et al., Science, 259, p.1739 (1993); B. D. Car et al., *J. Exp. Med.*, 179, p.1437 (1994)). Along with IL-12, IL-18 appears to be a potent inducer of IFN-γ production by T cells (H. Okamura et al., *Infection and Immunity*, 63, p.3966 (1995); H. Okamura et al., *Nature*, 378, p.88 (1995); S. Ushio et al., *J. Immunol.*, 156, p.4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

Accordingly, compositions and methods capable of regulating the conversion of pro-IL-18 to IL-18 would be useful for decreasing IL-18 and IFN-γ production in vivo, and thus for ameliorating the detrimental effects of these proteins which contribute to human disorders and diseases.

Caspase inhibitors represent a class of compounds useful for the control of inflammation or apoptosis or both. Peptide and peptidyl inhibitors of ICE have been described (PCT patent applications WO 91/15577, WO 93/05071, WO 93/09135, WO 93/12076, WO 93/14777, WO 93/16710, WO 95/35308, WO 96/30395, WO 96/33209 and WO 98/01133; European patent applications 503 561, 547 699, 618 223, 623 592, and 623 606'; and U.S. Pat. Nos. 5,434,248, 5,710,153, 5,716,929, and 5,744,451). Such peptidyl inhibitors of ICE have been observed to block the production of mature IL-1β in a mouse model of inflammation (vide infra) and to suppress growth of leukemia cells in vitro (Estrov et al., *Blood*, 84, 380a (1994)). However, due to their peptidic nature, such inhibitors are typically characterized by undesirable pharmacologic properties, such as poor cellular penetration and cellular activity, poor oral absorption, instability and rapid metabolism. Plattner, J. J. and D. W. Norbeck, in *Drug Discovery Technologies*, C. R. Clark and W. H. Moos, Eds. (Ellis Horwood, Chichester, England, 1990), pp.92-126. These properties have hampered their development into effective drugs.

Non-peptidyl compounds have also been reported to inhibit ICE in vitro. PCT patent application WO 95/26958; U.S. Pat. No. 5,552,400; Dolle et al., *J. Med. Chem.*, 39, pp. 2438-2440 (1996). It is not clear however whether these compounds have the appropriate pharmacological profiles to be therapeutically useful.

WO 99/47545 describes a novel class of caspase inhibitors reported to have a favorable in vivo profile. These inhibitors are represented by the formula:

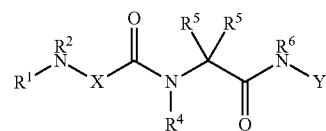

where X, Y, and $R^1$-$R^6$ are various substituents. Among the many examples of this class of inhibitors, the following structure was disclosed:

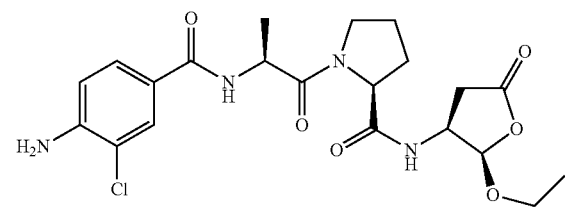

98d

As is known in the art, the bioavailability of compounds within a structural class is difficult to predict. Relatively minor structural modifications often have a large impact on the absorption of a compound, its blood level concentrations and/or its half-life. For example, such variations in bioavailability can be seen from the data in WO 99/47545. As a consequence, structurally related compounds that have very good in vitro potency may vary in therapeutic effectiveness.

Though progress has been made in improving the bioavailability of ICE inhibitors, there continues to be a need to identify and develop compounds that can effectively inhibit caspases, and that have improved in vivo activity. Such compounds would be useful as agents for preventing and treating chronic and acute forms of IL-1-, apoptosis-, IL-18-, or IFN-γ-mediated diseases, as well as inflammatory, autoimmune, destructive bone, proliferative, infectious, or degenerative diseases.

DESCRIPTION OF THE INVENTION

This invention provides a novel ICE inhibitor prodrug compound with surprisingly good bioavailability in mammals. The compound is represented by formula I:

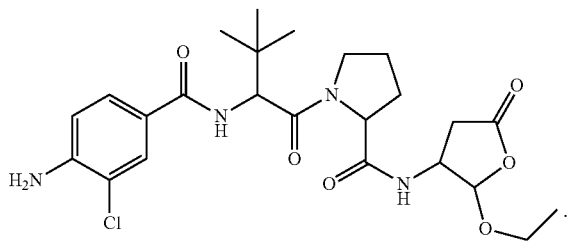

I

Compound I may be used alone or in combination with other therapeutic or prophylactic agents, such as antibiotics, immunomodulators or other anti-inflammatory agents, for the treatment or prevention of diseases mediated by IL-1, apoptosis, IL-18, or IFN-γ. This invention also relates to pharmaceutically acceptable derivatives and prodrugs of the compound.

Compound I itself is a prodrug that undergoes bioconversion to an active ICE inhibitor II:

I ⟶

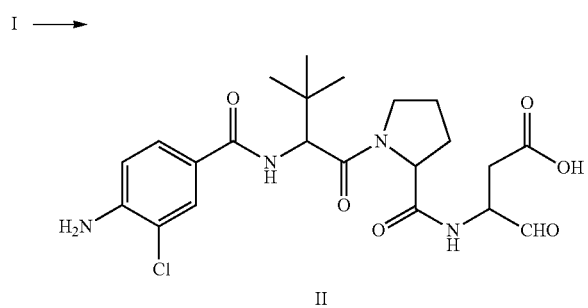

II

Compound I has better in vivo activity upon oral and/or intravenous administration than the parent or active form of the drug. The active form, aspartic aldehyde II, exhibits less than optimal in vivo activity, primarily because of poor bioavailability, and is therefore not well-suited for direct therapeutic use. Generally, poor bioavailability may result for any of the following reasons: the active form is not stable in the animal gut following ingestion, is not well-absorbed through the gut and/or is not well-delivered to the biological compartment (e.g., the brain or lymphatic system) for which it is intended. While the prodrug I shows enhanced bioavailability relative to its active form II, this invention is not limited to any particular mechanism by which the bioavailability is enhanced.

Applicants studied a number of prodrug ICE inhibitors, including examples listed in the aforementioned WO 99/47545. Bioavailability was determined by quantitating the amount of ICE inhibitor in rat plasma after oral administration, as described below. Compound I was found to have unexpectedly improved bioavailability relative to other prodrug ICE inhibitors tested, including some that were closely related in structure.

The structure for compound I depicted herein is meant to include all stereochemical forms of the compound; i.e., the R and S configurations for each asymmetric center. Therefore, single stereochemical isomers as well as enantiomeric and diastereomeric mixtures of the present compound are within the scope of the invention. A preferred isomer is compound I-A which has the "S" configuration at the carbon bearing the tert-butyl group, has the "S" configuration at the 2-position of the proline ring, has the "S" configuration at the 3-position of the furanone ring, and has the "R" configuration at the 2-ethoxy position of the furanone ring, as shown below:

I-A

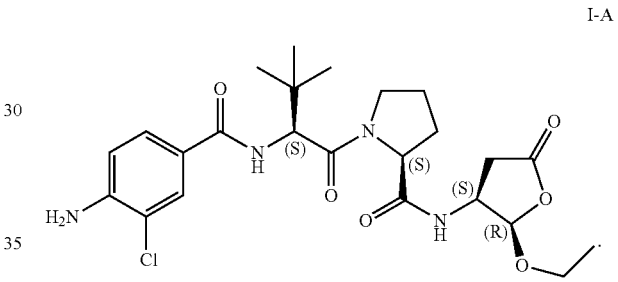

Another preferred isomer is compound I-B:

I-B

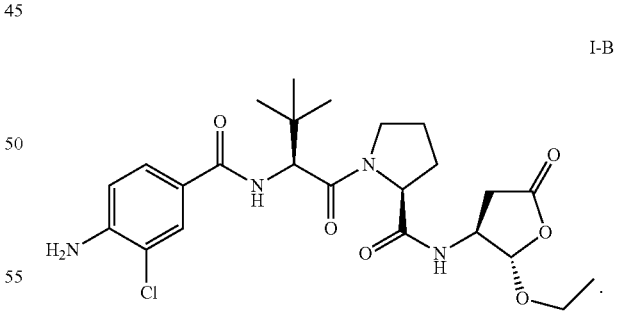

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

The compounds of this invention may be prepared in general by methods known to those skilled in the art for analogous compounds, as illustrated by the general scheme below and by the preparative examples below

Synthetic Scheme for Compound I-A

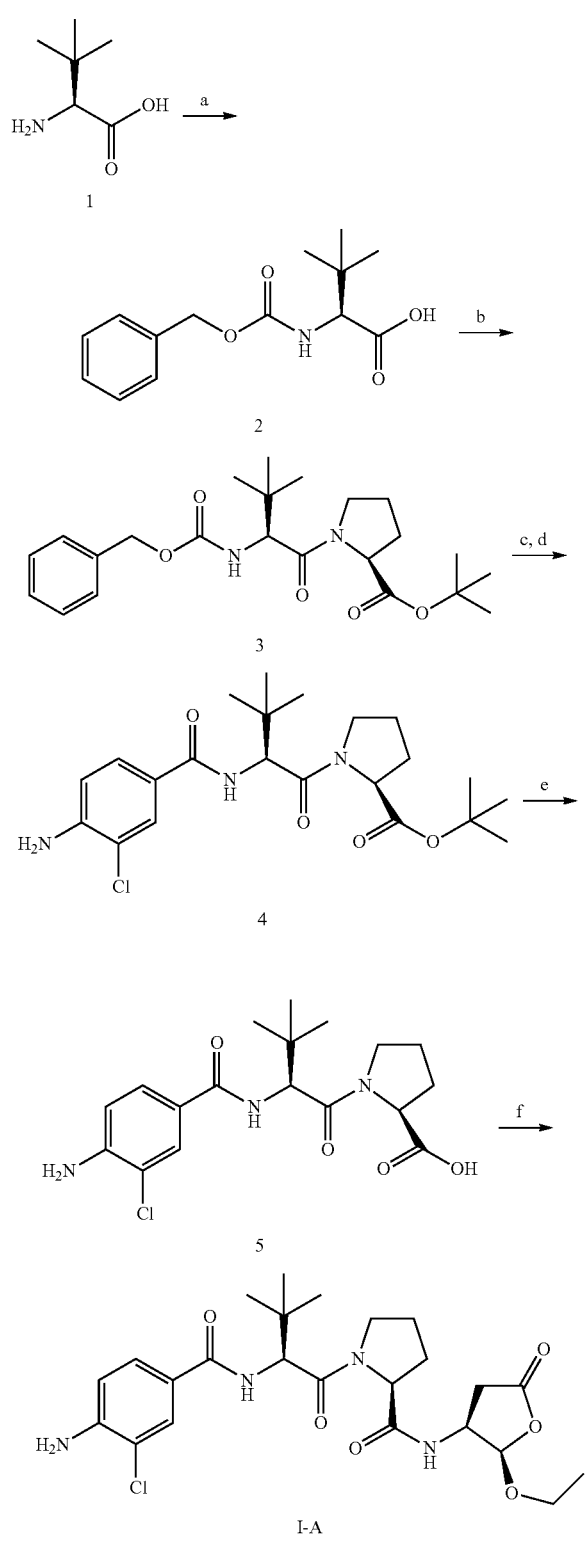

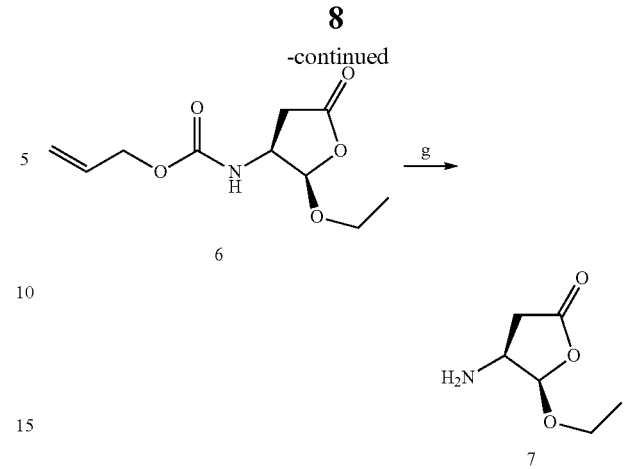

Reagents a) Cbz-Cl, NaHCO$_3$; b) H-Pro-OtBu, EDC, HOBT; c) 10% Pd/C, H$_2$; d) 4-amino-3-chlorobenzoic acid, EDC, DIPEA; e) TFA; f) 7, EDC, HOBT, DIPEA; g) DMBA, Pd(PPh$_3$)$_4$ Certain of the intermediates that are useful for making compound I are believed to be novel. Accordingly, one embodiment of this invention relates to compounds represented by formula II:

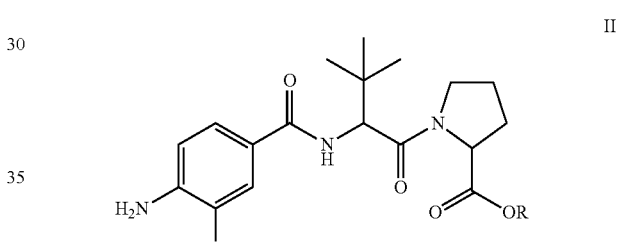

wherein R is selected from hydrogen or an organic radical, preferably hydrogen or a C$_{1-12}$ alkyl, and most preferably hydrogen or tert-butyl. It is understood that the organic radical moiety is a group that is unreactive toward the other functional groups in compound II. Compound II is understood to include any of the four possible stereoisomers, as well as mixtures thereof. A preferred isomer of II is represented by formula II-A:

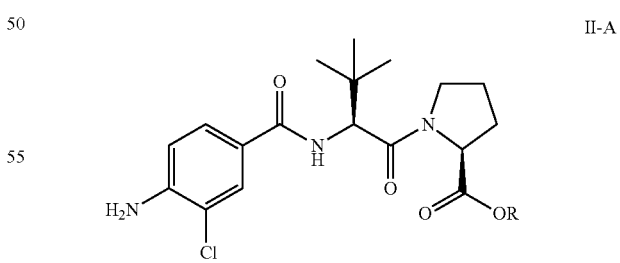

wherein R is as described above.

Pharmaceutical compositions of this invention comprise a compound of formula I or a pharmaceutically acceptable salt thereof and a pharmaceutically acceptable carrier. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as a-tocopherol, polyethyleneglycol 1000 succinate, or other Similar polymeric delivery matrices.

In pharmaceutical composition comprising only a compound of formula I as the active component, methods for administering these compositions may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating an IL-1-, apoptosis-, IL-18-, or IFN-γ-mediated disease in a patient. The term "prophylactically effective amount" refers to an amount effective in preventing or substantially lessening IL-1-, apoptosis-, IL-18-, or IFN-γ-mediated diseases in a patient.

The compounds of this invention may be employed in a conventional manner for controlling IL-18 and IFN-γ levels in vivo and for treating diseases or reducing the advancement or severity of effects which are mediated by IL-1, apoptosis, IL-18, or IFN-γ. Such methods of treatment, their dosage levels and requirements may be selected by those of ordinary skill in the art from available methods and techniques.

For example, a compound of this invention may be combined with a pharmaceutically acceptable adjuvant for administration to a patient suffering from an IL-1-, apoptosis-, IL-18-, or IFN-γ-mediated disease in a pharmaceutically acceptable manner and in an amount effective to lessen the severity of that disease.

Alternatively, the compounds of this invention may be used in compositions and methods for treating or protecting individuals against IL-1, apoptosis-, IL-18, or IFN-γ-mediated diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, IL-18, or IFN-γ-mediated diseases.

The compounds of formula I may also be co-administered with other caspase or ICE inhibitors to increase the effect of therapy or prophylaxis against various IL-1-, apoptosis-, IL-18-, or IFN-γ-mediated diseases.

In addition, the compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha-interferon antibody, IL-2, GM-CSF, methionine enkephalin, interferon-alpha, diethyldithiocarbamate, tumor necrosis factor, naltrexone and EPO), with prostaglandins, or with antiviral agents (e.g., 3TC, polysulfated polysaccharides, ganiclovir, ribavirin, acyclovir, alpha interferon, trimethotrexate and fancyclovir) or prodrugs of these or related compounds to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with, a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of IL-1-, apoptosis-, IL-18-, and IFN-γ-mediated diseases, including uveitis, inflammatory diseases, autoimmune diseases, destructive bone disorders, proliferative disorders, infectious diseases, degenerative diseases, necrotic diseases, inflammatory peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, myocardial infarction, congestive heart failure, Huntington's disease, atherosclerosis, spinal muscular atrophy, multiple sclerosis, AIDS-related encephalitis, HIV-related encephalitis, aging, alopecia, neurological damage due to stroke, ulcerative collitis, infectious hepatitis, juvenile diabetes, lichenplanus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

IL-1 or apoptosis mediated diseases which may be treated or prevented by the compounds of this invention include, but are not limited to, inflammatory diseases, autoimmune diseases, proliferative disorders, infectious diseases, and degenerative diseases. The apoptosis-mediated diseases which may be treated or prevented by the compounds of this invention include degenerative diseases.

IL-1 or apoptosis mediated inflammatory diseases which may be treated or prevented include, but are not limited to osteoarthritis, acute pancreatitis, chronic pancreatitis, asthma, and adult respiratory distress syndrome. Preferably the inflammatory disease is osteoarthritis or acute pancreatitis.

IL-1 or apoptosis mediated autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, atopic dermatitis and graft vs. host disease. Preferably the autoimmune disease is rheumatoid arthritis, inflammatory bowel disease, Crohn's disease, psoriasis, or atopic dermatitis.

IL-1 or apoptosis mediated destructive bone disorders which may be treated or prevented include, but are not limited to, osteoporosis and multiple myeloma-related bone disorder.

IL-1 or apoptosis mediated proliferative diseases which may be treated or prevented include, but are not limited to, leukemias and related disorders, such as myelodysplastic syndrome, acute myelogenous leukemia, chronic myelogenous leukemia, metastatic melanoma, Kaposi's sarcoma, and multiple myeloma.

IL-1 or apoptosis mediated infectious diseases which may be treated or prevented include, but are not limited to, sepsis, septic shock, and Shigellosis.

IL-1 or apoptosis mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

IL-1 or apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated or prevented by the compounds of this invention. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

IL-18- or IFN-γ-mediated diseases which may be treated or prevented by the compounds of this invention include, but are not limited to, inflammatory, infectious, autoimmune, proliferative, neurodegenerative and necrotic conditions.

IL-18- or IFN-γ-mediated inflammatory diseases which may be treated or prevented include, but are not limited to osteoarthritis, acute pancreatitis, chronic pancreatitis, asthma, rheumatoid arthritis, inflammatory bowel disease, Crohn's disease, ulcerative collitis, cerebral ischemia, myocardial ischemia and adult respiratory distress syndrome. Preferably, the inflammatory disease is rheumatoid arthritis, ulcerative collitis, Crohn's disease, hepatitis or adult respiratory distress syndrome.

IL-18- or IFN-γ-mediated infectious diseases which may be treated or prevented include, but are not limited to infectious hepatitis, sepsis, septic shock and Shigellosis.

IL-18- or IFN-γ-mediated autoimmune diseases which may be treated or prevented include, but are not limited to glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease or hepatitis.

More preferred diseases or conditions which may be treated or prevented include rheumatoid arthritis, inflammatory bowel disease, including Crohn's disease and ulcerative colitis, inflammatory peritonitis, amyotrophic lateral sclerosis, septic shock, pancreatitis, traumatic brain injury, organ transplant rejection, osteoporosis, osteoarthritis, asthma, uveitis, psoriasis, Alzheimer's disease, myocardial infarction, congestive heart failure, Huntington's disease, atherosclerosis, atopic dermatitis, or leukemias and related disorders, such as myelodysplastic syndrome or multiple myeloma.

Accordingly, one embodiment of this invention provides a method for treating or preventing an IL-1 or apoptosis mediated disease in a subject comprising the step of administering to the subject any compound, pharmaceutical composition, or combination described herein and a pharmaceutically acceptable carrier.

Another embodiment of this invention provides a method for decreasing IL-18 production in a subject comprising the step of administering to the subject any compound, pharmaceutical composition, or combination described herein and a pharmaceutically acceptable carrier.

Yet another embodiment of this invention provides a method for decreasing IFN-γ production in a subject comprising the step of administering to the subject any compound, pharmaceutical composition, or combination described herein and a pharmaceutically acceptable carrier.

Although this invention focuses on the use of the compounds disclosed herein for preventing and treating IL-1, apoptosis-, IL-18, and IFN-☐-mediated diseases, the compounds of this invention can also be used as inhibitory agents for other cysteine proteases.

The compounds of this invention are also useful as commercial reagents which effectively bind to caspases or other cysteine proteases including, but not limited to ICE. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for. the purpose of illustration only and are not to be construed as limiting the scope of the invention in any way.

Synthetic Examples

Preparation of 1-[2-(4-amino-3-chloro-benzoylamino)-3,3-dimethyl-butyryl]-pyrrolidine-2-carboxylic acid (2-ethoxy-5-oxo-tetrahydro-furan-3-yl)-amide (I-A)
2-Benzyloxycarbonylamino-3,3-dimethyl-butyric acid (2)
To a solution of L-tert-leucine (1) (50.0g, 38.0 mmol) and NaHCO$_3$ (96.0g, 114 mmol) in ice (500g) and water (500 ml) was added benzyl chloroformate (65.0 ml, 74.0 mmol) and the reaction stirred at 0° C. for 3 hours then at room temperature for 18 hours. 0.1N Na$_2$CO$_3$ was added until the oily layer dissolved and the solution was washed with 10% EtOAc in hexanes (2×500 ml). The iced aqueous phase was acidified to pH 1 using 12N HCl then extracted using EtOAc (3×350 ml). The combined organic extracts were dried over Na$_2$SO$_4$, filtered and evaporated to give the title compound as a colorless oil (82.4g, 81.5% yield): $^1$H-NMR (500 MHz, CDCl$_3$) δ1.02 (s, 9H), 4.22 (d, 1H), 5.10-5.14 (m, 2H), 5.31 (d, 1H), 7.26-7.37 (m, 5H).

1-(2-Benzyloxycarbonylamino-3,3-dimethyl-butyryl)-pyrrolidine-2-carboxylic acid tert-butyl ester (3)

To a solution of 2 (6.01g, 2.0 mmol) in CH$_2$Cl$_2$ (30 ml) and anhydrous DMF (dimethylformamide) (10 ml) at 0° C. was added HOBT (3.16 g, 2.0 mmol), EDC (1-(3-dimethylaminopropyl-3-ethyl-carbodiimide hydrochloride) (7.19 g, 4.0 mmol) and L-proline-tert-butyl ester (4.22 g, 2.0 mmol). The solution was stirred at 0° C. for 10 minutes, then at room temperature for 5 hours. The solvents were evaporated in-vacuo and the resulting oil dissolved in EtOAc which was washed with H$_2$O (3×200 ml) and brine (200 ml). The organic phase was dried over anhydrous Na$_2$SO$_4$, filtered and evaporated to give the crude product. Flash chromatography on silica gel using hexanes/EtOAc (95/5 to 80/20%) afforded the title compound as a colorless oil (8.30 g, 87.5% yield): $^1$H-NMR (500 MHz, CDCl$_3$) □ 1.04 (s, 9H), 1.45 (s, 9H), 1.89-1.96 (m, 2H), 2.02-2.05 (m, 1H), 2.18-2.22 (m, 1H), 3.65-3.69 (m, 1H), 3.79-3.82 (m, 1H), 4.34-4.37 (m, 2H), 5.03-5.19 (m, 2H), 5.53 (d, 1H), 7.26-7.38 (5H).

Synthesis of 1-[2-(4-amino-3-chloro-benzoylamino)-3,3-dimethyl-butyryl]-pyrrolidine-2-carboxylic acid tert-butyl ester (4).

To a solution of 3 (19.0 g, 45.4 mmol) in MeOH (200 mL) was added 10% activated Pd on C (2.0 g) in EtOAc (50 mL) and the reaction stirred under H$_2$ for 18 hours. The solution was filtered through Celite and the solvent evaporated to yield a viscous, colorless oil. The free amine was dissolved in dry CH$_2$Cl$_2$/DMF (2:1, 120 mL), the solution cooled to 0° C. and 4-amino-3-chlorobenzoic acid (7.79 g, 45.4 mmol) and DIPEA (7.90 mL, 45.4 mmol) were added. The reaction was stirred for 10 minutes, then EDC (11.32 g, 59.1 mmol) was added. The mixture was stirred at 0° C. for 30 minutes then at room temperature for 18 hours. The solution was diluted with EtOAc (300 mL), washed with 0.5N NaHSO$_4$ (2×250mL), 10% NaHCO$_3$ (2×250 mL), saturated NaCl (150 mL), dried over MgSO$_4$, and evaporated to dryness. Flash column chromatography on silica gel using CH$_2$Cl$_2$/MeOH, (99/1 to 98/2%) yielded the title compound as a white solid (19.25 g, 97% yield): $^1$H-NMR (500 MHz, CDCl$_3$) δ 1.12 (s, 9H), 1.48 (s, 9H), 1.85-1.99 (m, 2H), 2.01-2.13 (m, 1H), 2.18-2.29 (m, 1H), 3.63-3.73 (m, 1H), 3.84-3.93 (m, 1H), 4.30-4.41 (m, 1H), 4.86 (d, 1H), 6.73 (d, 1H), 7.51 (d, 1H), 7.73 (s, 1H). Analytical HPLC (cyano column): 12.59 min. LC-MS (ES+) m/e=438.5 (M+H).

Synthesis of 1-[2-(4-amino-3-chloro-benzoylamino)-3,3-dimethyl-butyryl]-pyrrolidine-2-carboxylic acid (5).

To a solution of 4 (15.9 g, 36.3 mmol) in CH$_2$Cl$_2$ (30 mL) was added TFA (trifluoroacetic acetic acid) (30 mL) and the solution stirred at room temperature for 3 hours under N$_2$. The reaction was transfered to a beaker (1 L) and diluted with CH$_2$Cl$_2$ (60 mL). To the solution at 0° C. was added solid NaHCO$_3$ (39 g, 46 mmol) and stirred for 15 minutes before partitioning between EtOAc (300 mL) and H$_2$O (300 mL). After extraction the aqueous layer was acidified to pH 4-5 and extracted with EtOAc. The organic layer was dried (MgSO$_4$) and evaporated to dryness to give 5 as a white solid (14.0 g, quantitative yield): $^1$H-NMR (500 MHz, CDCl$_3$) δ1.08 (s, 9H), 1.97-2.22 (m, 3H), 2.29-2.41 (m, 1H), 3.71-3.78 (m, 1H), 3.90-3.98 (m, 1H), 4.55-4.62 (m, 1H), 4.86 (d, 1H), 6.64 (d, 1H), 6.74 (d, 1H), 7.53 (d, 1H), 7.74 (s, 1H). Analytical HPLC (cyano column): 8.24 min. LC-MS (ES+) m/e=382.4 (M+H).

Synthesis of 1-[2-(4-amino-3-chloro-benzoylamino)-3,3-dimethyl-butyryl]-pyrrolidine-2-carboxylic acid (2-ethoxy-5-oxo-tetrahydro-furan-3-yl)-amide (I-A).

To a solution of 6 (5.05 g, 22.0 mmol) in CH$_2$Cl$_2$ (50 mL) at 0° C. was added 1,3-dimethylbarbituric acid (DMBA) (3.78 g, 24.2 mmol)and Pd(PPh$_3$)$_4$ (0.15 g, 0.13 mmol). After 10 minutes, a solution of 5 (8.40 g, 22.0 mmol) in DMF (25 mL) was added followed by diisopropylethylamine (DIPEA) (7.66 mL, 44.1 mmol), (2.98 g, 22.0 mmol) and EDC (5.06 g, 26.4 mmol). The solution was stirred at 0° C. for 10 minutes then at room temperature for 18 hours. The reaction was diluted with EtOAc (200 mL), washed with 0.5N NaHSO$_4$ (2×200 mL), 10% NaHCO$_3$ (2×200 mL), saturated NaCl (1×150 mL), dried over anhydrous MgSO$_4$, and evaporated to dryness. Flash column chromatography on silica gel using CH$_2$Cl$_2$/MeOH, (99/1 to 98/2%) afforded the title compound as a white solid (11.20 g, 77% yield): $^1$H-NMR (500 MHz, CDCl$_3$) δ 1.08 (s, 9H), 1.27 (t, 3H), 1.85-1.99 (m, 1H), 2.00-2.06 (m. 1H), 2.07-2.18 (m, 1H), 2.32-2.48 (m, 2H), 2.78-2.89 (m, 1H), 3.62-3.76 (m, 2H), 3.82-3.96 (m, 2H), 4.39 (s, 1H), 4.54-4.60 (m, 1H), 4.62-4.76 (m, 1H), 4.85 (d, 1H), 6.57 (d, 1H), 6.73 (d, 1H), 7.38 (d, 1H), 7.49 (d, 1H), 7.72 (s, 1H). Analytical HPLC (cyano column): 13.10 min. LC-MS (ES$^+$) m/e=509.4 (M+H), m.p.=96-99° C.

Oral Pharmacokinetic Studies

Male Sprague-Dawley rats (Harlan, Indianapolis, Ind., 300-350 g) were anesthetized by an intramuscular injection of ketamine/rompun mixture. A PE-50 cannula was inserted in the right carotid artery for arterial blood sampling. The rats were allowed to recover from surgery overnight (16 hours) prior to being used in the study. Test compounds were administered orally at 50 mg/kg 100% propylene glycol (PG).at a dose volume of 10 mL/kg. Blood samples (~0.30 mL) were removed at 0.25, 0.50, 1.0, 1.5, 2, 3, 4, 6, and 8 hours post-dose, plasma separated by centrifugation and stored at −80° C. pending analysis. Quantification of the plasma samples was conducted using a gradient HPLC/MS/MS similar to the one detailed below:

HPLC/MS/MS Method for the quantitation of ICE inhibitors in rat plasma

Sample Preparation 1. 100 μl of plasma are aliquotted into Ependorf centrifuge vials.

2. An equal volume of acetonitrile is added to the plasma to precipitate plasma proteins.

3. Samples are vortexed for 2 minutes, and centrifuged at 14,000 rpms for 3 minutes.

4. 100 μl of the supernatant is loaded into 12 mm HPLC liquid sampler vials.

5. A 20 μl addition of external standard is added to the 100 μl aliquot to monitor variation in instrumental response.

6. 10 μl of sample is injected for analysis via the mass spectrometer.

HPLC Instrumental Parameters

HPLC: Hewlett Packard HP1100 Binary Solvent Delivery System.

HPLC Gradient Conditions

A=H$_2$O 0.2% Formic Acid

B=Acetonitrile 0.2% Formic Acid

Mobile Phase

| Time (min) | % A | % B |
| --- | --- | --- |
| 0 | 100 | 0 |
| 2 | 100 | 0 |
| 5 | 0 | 100 |
| 11 | 0 | 100 |
| 11.5 | 100 | 0 |
| 15 | 100 | 0 |

HPLC Analytical Column: Keystone Phenyl −1 Hypersil 2.0×100 mm, 5 μ 120 Å pore pore size, P/N# 105-36-2
Injection Volume: 10 μl
Flow Rate: 0.20 mL/min.

Mass Spectrometry Instrumental Parameters
Instrument: Micromass Quattro Ultima, Tandem Mass. Spectrometer
Ionization Technique: Orthogonal spray (ESI)
Polarity: Positive
Dwell Time: 300 msec
Pause Time: 5 msec
Scan time: 0.9 sec
Scan Mode: MRM (Multiple Reaction Monitoring)
Ions/Transitions: For compound I-A m/z509.1-243.1
    For compound II m/z481.1-215.1
Pharmacokinetic Parameters Pharmacokinetic analysis of these plasma concentration data was conducted using noncompartmental methods. The area under the curve ($AUC_{(0-t)}$0-t) was estimated from time zero to the last measured time point using the linear trapezoidal rule. The rate of elimination (ke) was estimated by log-linear regression from the terminal phase of the plasma concentration-time curves. Area under the tail of the curve was estimated as the ratio of the last measured concentration to ke. The area under the curve from time zero to infinity (AUC(0-∞)) was obtained by addition of the area under the tail to AUC(0-t). Elimination half-life was estimated as 0.693/ke. The observed values for the peak plasma concentration (Cmax) were recorded.

TABLE 1

Oral Pharmacokinetic Data

| Example | Cmax (μg/mL) | AUC (μgXh/mL) | t 1/2 (hrs) |
| --- | --- | --- | --- |
| Compound A | 1.8 | 2.18 | 2.9 |
| Compound B | 0.51 | 1.35 | 0.25 |
| Compound I | 4.27 | 11.7 | 2.5 |

Table 1 above compares the pharmacokietic values of compound I with compounds A and B that are closely related in structure. As can be seen from the data, Cmax and AUC are much higher for compound I than for the other two compounds.

While we have described a number of embodiments of this invention, it is apparent that our basic constructions may be altered to provide other embodiments that utilize the products and processes of this invention.

We claim:
1. A compound represented by formula II:
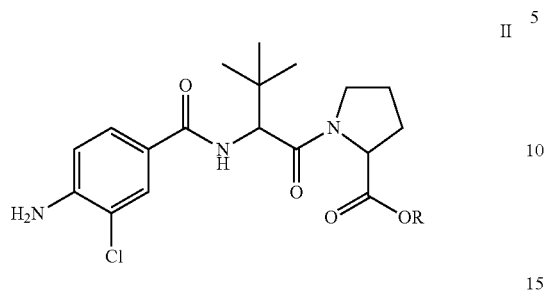
wherein R is selected from hydrogen or an organic radical.
2. The compound of claim 1 wherein R is selected from hydrogen or tert-butyl.
* * * * *